(12) United States Patent
Murata (10) Patent No.: US 6,399,957 B1
(45) Date of Patent: Jun. 4, 2002

(54) METHOD AND APPARATUS FOR INSPECTING APPEARANCE OF OBJECTS BY IRRADIATING ILLUMINATION LIGHT ON THE OBJECTS

(75) Inventor: Koji Murata, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/447,255

(22) Filed: Nov. 23, 1999

(30) Foreign Application Priority Data

Nov. 30, 1998 (JP) .......................................... 10-340801

(51) Int. Cl.$^7$ .............................................. G01N 21/88
(52) U.S. Cl. .................................. 250/559.4; 356/237.4
(58) Field of Search .......... 250/539.45, 539.03–559.49, 250/221, 222.1, 222; 356/237.1–237.6, 429–431, 337–343

(56) References Cited

U.S. PATENT DOCUMENTS 5,625,193 A * 4/1997 Broude et al. .............. 250/372

FOREIGN PATENT DOCUMENTS

| JP | 5-109849 | | 4/1993 |
| JP | 8-75661 | | 3/1996 |
| JP | 10-232122 A | * | 9/1998 |

* cited by examiner

Primary Examiner—Que T. Le
Assistant Examiner—Thanh X. Luu
(74) Attorney, Agent, or Firm—Oliff & Berridge, PLC (57) ABSTRACT

An appearance inspection method of the invention comprises: a first step for inspecting an object to be inspected by illuminating the object to be inspected mounted on a first stage and receiving scattered light therefrom, a second step for inspecting the object to be inspected by illuminating the object to be inspected mounted on a second stage and receiving diffracted light therefrom, and a transfer step for transferring the object to be inspected between the first stage and the second stage so that either one of the first step and the second step is carried out after the other. As a result, with this appearance inspection method, it is possible to prevent a lengthening in the throughput time even when a plurality of inspections are automatically carried out, while maintaining the same functions as for conventional inspection which is carried out visually.

9 Claims, 7 Drawing Sheets

METHOD AND APPARATUS FOR INSPECTING APPEARANCE OF OBJECTS BY IRRADIATING ILLUMINATION LIGHT ON THE OBJECTS

BACKGROUND OF THE INVENTION

1. Field of the Invention

The present invention relates to an appearance inspection method and appearance inspection apparatus for performing appearance inspection for uneven exposure, de-focusing, poor coating, scratches, and the like of an inspection object, by irradiating illumination light on objects to be inspected such as substrates which are used in the production of micro devices such as semiconductor elements, imaging elements (CCDs, etc.) liquid crystal displays and thin film magnetic heads.

2. Description of the Related Art

Recently with the advance in high integration of semiconductor devices, in the fields of inspection and measurement, the resolution which is required with respect to inspection devices for observing and inspecting for defects in patterns on wafers and reticules has followed continual refinements with each successive generation.

Despite the low level of demand for improvements in resolution for inspection in the area of appearance inspection for inspecting for uneven coating, uneven exposure, de-focusing, poor coating, scratches and the like of resist on a wafer, the importance which is being placed on reducing production costs has resulted in expectations for realizing an automated inspection device for automatically carrying out the aforementioned appearance inspections which have heretofore relied upon visual inspection.

In the past, for this kind of appearance inspection apparatus, a method is adopted where the entire wafer surface being the object to be inspected, on an inspection stage, is illuminated with a uniform light source, and the entire wafer surface is photographed at one time using a two-dimensional camera and taken as an inspection image. Furthermore, Japanese Patent Application, First Publication No. 8-75661, discloses a method for inspecting for defects such as scratches, impurities and stains on substrates, by receiving diffracted light from repeated patterns on the substrate.

Since when a substrate is inspected according to this method, the same level of throughput is required as with a conventional inspection carried out visually by a trained inspector, it is necessary for example, to make the amount of time taken to photograph an image of the substrate the same as that taken in a visual inspection. Hence, the method of photographing the entire substrate at the same time has recently been adopted in an attempt to increase throughput.

However, the following type of problems are to be found with regard to the aforementioned conventional appearance inspection methods and appearance inspection apparatuses.

The detection of the above-mentioned defects differs greatly according to the type of fault. For instance, in the inspection for impurities and scratches on the surface of the object to be inspected, through the use of light illumination, scattered light emanating from a defect on the surface being inspected is utilized. Additionally, in the inspection for uneven coating, uneven exposure, de-focusing and poor coating on the resist, the diffracted light which is generated from the object to be inspected by light illumination is used.

What is more, the main objective of automating an inspection which has until now relied upon visual inspection, necessitates the implementation of an inspection which follows the inspection procedure which has heretofore been carried out by an inspector. Accordingly, it is necessary to follow in order the several inspection steps which, with conventional appearance inspection methods and appearance inspection apparatuses, entail such things as separately photographing the substrates in accordance with the aforementioned various inspection procedures. Hence there is the disadvantage that inspection throughput time is increased.

SUMMARY OF THE INVENTION

The present invention takes into consideration the above points with the object of providing an appearance inspection method and an appearance inspection apparatus which has the ability to shorten the inspection throughput time, even when carrying out automatically the same inspection as that carried out visually.

In order to achieve the above objective, an appearance inspection method according to the present invention is characterized in comprising: a first step for inspecting an object to be inspected by illuminating the object to be inspected mounted on a first stage and receiving scattered light therefrom, a second step for inspecting the object to be inspected by illuminating the object to be inspected mounted on a second stage and receiving diffracted light therefrom, and a transfer step for transferring the object to be inspected between the first stage and the second stage so that either one of the first step and the second step is carried out after the other.

Accordingly, with the appearance inspection method of the present invention, in the case where the object to be inspected is a substrate which has been coated with resist, then while inspecting in the first step for scratches and impurities on the surface of the object to be inspected using the scattered light generated from the object to be inspected on the first stage, it is possible to inspect concurrently in the second step for uneven coating, uneven exposure, de-focusing and poor coating on the resist using the diffracted light generated from the object to be inspected on the second stage. Furthermore, when either one of the first step or the second step is completed, then in the transfer step the object to be inspected is transferred between the first stage and the second stage. After this, the inspection of the other step is carried out on the transferred object to be inspected.

As a result, with this appearance inspection method, the effect is obtained that it is possible to prevent a lengthening in the throughput time even when a plurality of inspections are automatically carried out, while maintaining the same functions as for the conventional inspection which is carried out visually.

With an appearance inspection method of an embodiment of the present invention, in accordance with the transfer by the transfer step of the object to be inspected from one stage of either the first stage and the second stage, a new object to be inspected is transferred to the one stage.

According to this appearance inspection method, it is possible to simultaneously execute the first step and the second step concurrently, enabling a substantial improvement in the inspection throughput.

With an appearance inspection method of another embodiment of the present invention, prior to inspection of the object to be inspected, an alignment step is carried out for aligning the object to be inspected at a predetermined location by moving a stage.

According to this appearance inspection method, it is possible to perform inspection at the optimum position corresponding to the object to be inspected, and thereby improve inspection accuracy. Furthermore, the inspection not only makes it possible to detect the presence of defects, but also enables the coordinate position where the defects occurs to be specified. Therefore, it is easy to undertake a subsequent so-called micro inspection for making a concentrated inspection of the region.

With an appearance inspection method of another embodiment of the present invention, after completion of one step of the first and second steps, the object to be inspected is pre-aligned to a direction required for the other step, while remaining mounted on the stage used for the one step, after which the object to be inspected is transferred to the stage of the other step by the transfer step.

According to this appearance inspection method, inspection at the optimum position corresponding to the object to be inspected is also possible in the other step, enabling an improvement in inspection accuracy. Furthermore, as with the first inspection, it is possible to specify the coordinate position where the defect occurs, and hence post inspection micro inspection can be easily performed. In addition, since it is no longer necessary to provide a separate mechanism for alignment for the stage which is used in the second step, it is possible to also realize device miniaturization and a reduction in costs.

With an appearance inspection method of another embodiment of the present invention, a plurality of long inspection time steps are carried out concurrent with a short step, and transfer is carried out so that the object to be inspected which has just completed the long step is transferred to the short step by turns.

According to this appearance inspection method, it is possible to set the period for performing the short inspection time step on the short inspection time side without needing to match this with the period for performing the long inspection time step, thereby enabling a further reduction in throughput time.

With an appearance inspection method of another embodiment of the present invention, based on the inspection results for the object to be inspected in one step, an inspection mode for the other step is changed.

According to this appearance inspection method, since it is possible in the other step to set an additional inspection in addition to the usual inspection, and to perform a concentrated inspection of parts where defects are likely, it is possible to reliably detect even smaller defects, thereby enabling an improvement in inspection accuracy.

With an appearance inspection method of another embodiment of the present invention, based on the inspection results for the object to be inspected in one step, a decision is made to either execute or cancel the other step.

According to this appearance inspection method, it becomes possible to cancel a redundant step where inspection is performed in the other step with respect to an object to be inspected which is not suitable for use, thus enabling an improvement in throughput.

With an appearance inspection method of another embodiment of the present invention, in the case where the other step is cancelled based on the inspection results for the object to be inspected in the one step, the object to be inspected is transferred by way of the stage used in the other step.

According to this appearance inspection method, inspection can be performed as prescribed without interrupting the sequence of the transfer of the object to be inspected.

As for the appearance inspection apparatus of the present invention, this comprises: a first stage for inspecting an object to be inspected by illuminating the object to be inspected and receiving scattered light therefrom, a second stage for inspecting the object to be inspected by illuminating the object to be inspected and receiving diffracted light therefrom, and a transfer mechanism for transferring the object to be inspected between the first stage and the second stage so that either one of the inspection of the first stage and the inspection of the second stage is carried out after the other.

According to the appearance inspection apparatus of the present invention, while inspecting for scratches and impurities on the surface of the object to be inspected using the scattered light generated from the object to be inspected on the first stage, it is possible to inspect concurrently for uneven coating, uneven exposure, de-focusing and poor coating on the resist using the diffracted light generated from the object to be inspected on the second stage. Furthermore, when either one of the inspections of the inspections on the two stages is completed, the transfer mechanism transfers the object to be inspected between the first stage and the second stage. The inspection on the other stage is then carried out on the transferred object to be inspected. As a result, it is possible to prevent a lengthening in the throughput time even when a plurality of inspections are automatically carried out, while maintaining the same functions as for the conventional inspection which is carried out visually.

With an appearance inspection apparatus of another embodiment of the present invention, the alignment mechanism is constructed so as to perform alignment of the object to be inspected by moving the first stage or the second stage.

According to this appearance inspection apparatus, it is possible to perform inspection at the optimum position corresponding to the object to be inspected, and thereby improve inspection accuracy. Furthermore, the inspection not only makes it possible to detect the presence of defects, but also enables the coordinate position where the defects occurs to be specified. Therefore, it is easy to undertake a subsequent so-called micro inspection for making a concentrated inspection of the region.

With an appearance inspection apparatus of a further embodiment of the present invention, the construction is such that the illumination light used for the first stage and the illumination light used for the second stage share a single light source.

According to this appearance inspection apparatus, since the number of light sources is reduced, it possible to realize device miniaturization and a reduction in costs.

DESCRIPTION OF THE PREFERRED EMBODIMENTS

Hereunder, a first embodiment of an appearance inspection method and an appearance inspection apparatus of the present invention will be explained with reference to FIG. 1 through FIG. 5. Here, the object to be inspected will be described as a wafer used for example in the manufacture of semiconductor devices, and the appearance inspection apparatus will be described in the context of it being used in an inspection step which takes place at the time of semiconductor manufacture.

Figure 1:
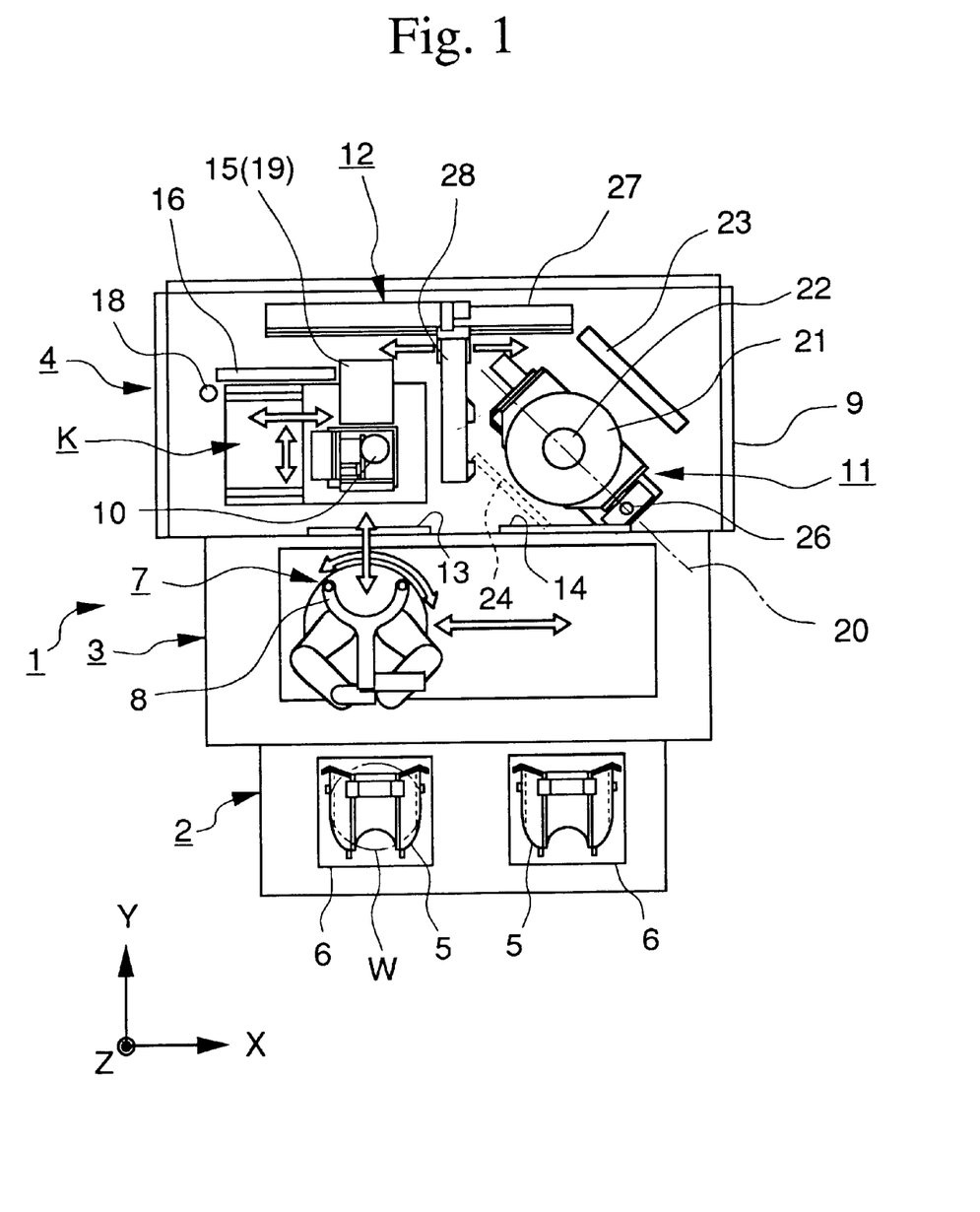
FIG. 1 is a diagram showing a first embodiment of the present invention, being a plan view of an appearance inspection apparatus equipped with a scattering inspection stage, a diffraction inspection stage and a transfer slider.

FIG. 1 is a plan view of the appearance inspection apparatus 1 of the present invention. The appearance inspection apparatus 1 inspects the outside of a wafer W (object to be inspected) and has a carrier set section 2, a transfer section 3 and an inspection section 4, arranged in consecutive order in a line in one direction (Y direction).

The carrier set section 2 is a location where there is set carriers 5 which are able to store a plurality of wafers W (for example 25), and is constructed with a plurality of support bases 6 (two bases in the figure) spaced apart in the X direction, for supporting the carriers 5 in located conditions.

The transfer section 3 is fitted with a scalar-type transfer robot 7 which has a suction attachment arm 8. The transfer robot 7 transfers the wafer W between the support base 6 and the inspection section 4 and moves freely in a vertical direction (Z direction) and also to the left and right direction (X direction) along which the support bases 6 are aligned, and moreover rotates and extends and contracts freely along the XY plane.

The inspection section 4 comprises; a body cover 9, a scattering inspection stage 10 (first stage) which is positioned within the body cover 9, a diffraction inspection stage 11 (second stage), and a transfer slider 12 (transfer mechanism). A wall surface on the transfer section 3 side of the body cover 9 is fitted with an aperture (not shown) and also shutters 13 and 14 which open and close freely.

The shutter 13 is positioned facing the scattering inspection stage 10. Furthermore, the shutter 14 is positioned facing the diffraction inspection stage 11. The shutters 13 and 14 open when the wafer W is being transferred by the transfer robot 7 and close when the inspection image is being taken, thereby cutting off the light within the body cover 9 at the time of inspection so as to maintain a darkened condition.

The scattering inspection stage 10 is for mounting the wafer W when executing so called scattering inspection where the wafer W is illuminated, and defects on the surface of the wafer W are inspected by receiving the scattered light which is generated by these defects. By means of a rotation mechanism, an elevation shaft and a dual axis horizontal shift mechanism, the scattering inspection stage 10 can be freely rotated, freely moved along the X-Y plane in the horizontal direction and freely moved up and down. The scattering inspection stage 10 is made so that it supports a central part of the under side of the wafer W for the purpose of pre-alignment. Furthermore, affixed in close proximity to the scattering inspection stage 10 are an alignment mechanism 15 to be described later, and a light source 16, a concave mirror 17 and a CCD camera 18 (photographing device), all of which are shown in FIG. 2.

The alignment mechanism 15 shown in FIG. 1 is for aligning (pre-aligning) the transferred wafer W prior to the scattering inspection, and comprises of an edge detection section 19 and a stage control section (not shown). When the scattering inspection stage 10 rotates, the edge detection section 19 detects the direction and central position of the wafer W by detecting the position of a notch or an orientation flat formed on the wafer W.

The stage control section controls the movement of the scattering inspection stage on the basis of the detection result from the edge detection section 19. More specifically, it controls the scattering inspection stage 10 based on the detection result from the edge detection section 19 so that the wafer W has a prescribed direction, and so that the wafer W is moved to a predetermined position of an inspection position K which is provided in close proximity to the edge detection section 19. This stage control section is controlled by a main control section (not shown) which generally controls the drive of the transfer robot 7, the transfer slider 12, the diffraction inspection stage 11 and the like.

Figure 2:
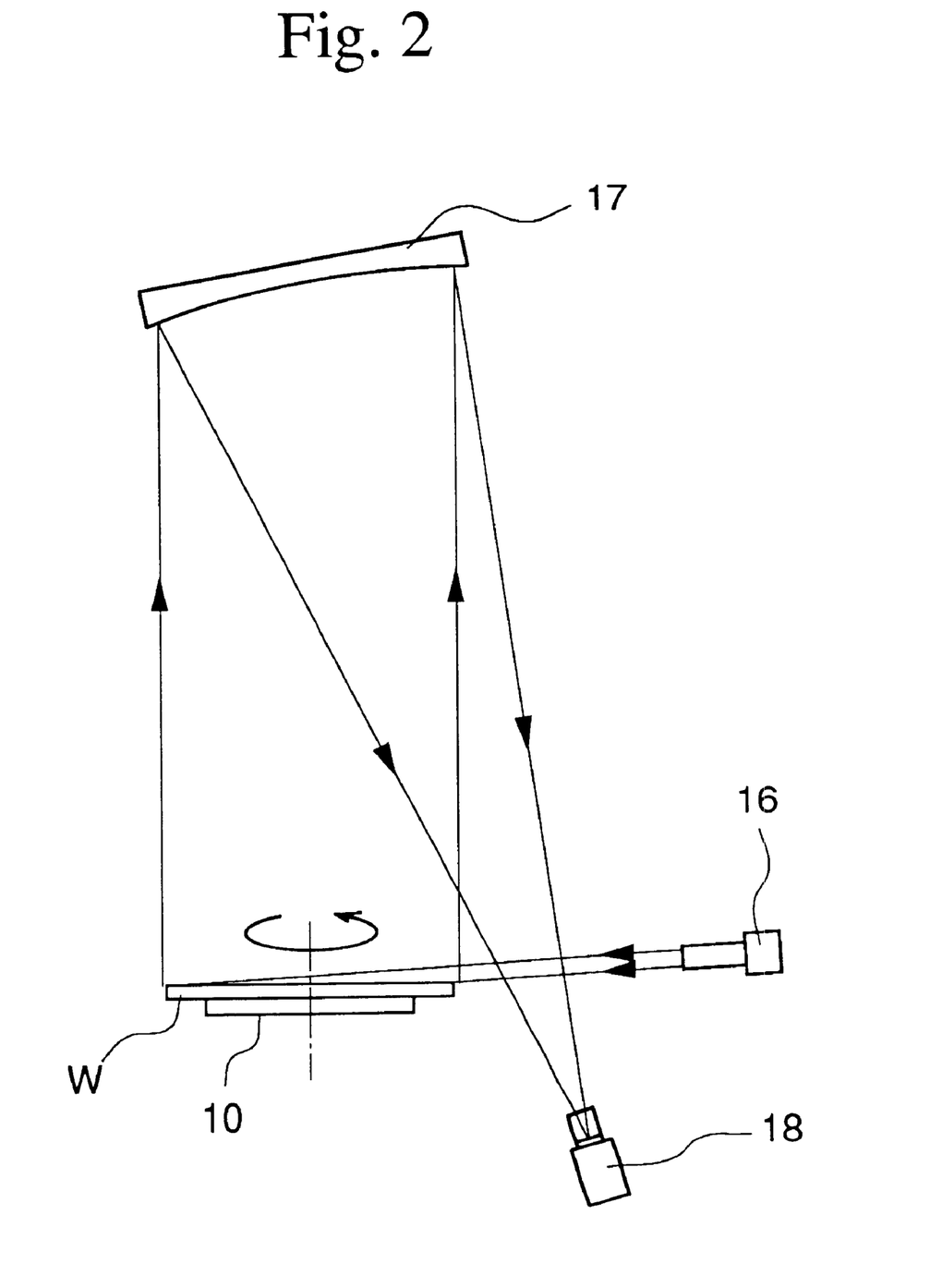
FIG. 2 is a front view showing the same scattering inspection stage provided with a light source, a concave mirror and a CCD camera.

FIG. 2 is a diagram showing the positioning of the scattering inspection stage 10, the light source 16, the concave mirror 17 and the CCD camera 18.

The light source 16 comprises of a metal hydride lamp or the like, which projects white light (illumination light), and as shown in FIG. 1 is located in a position such that the white light is incident at a slight angle with respect to the top surface, that is the horizontal surface of the scattering inspection stage 10 which is in the inspection position K.

The concave mirror 17 is positioned above the inspection position K and reflects so that the scattered light which is generated when the light source 16 shines towards the wafer W is imaged at the CCD camera 18. The CCD camera 18 is for photographing the scattered light which is reflected by the concave mirror 17.

The diffraction inspection stage 11 is for mounting the wafer W when executing so called diffraction inspection where the wafer W is illuminated and defects on the surface of the wafer W are inspected by receiving diffraction light from repeated patterns on the wafer W. The diffraction inspection stage 11 principally comprises a holder 21 for holding the wafer W and an elevation mechanism 22. Furthermore, a tilting mechanism (not shown) is attached to the diffraction inspection stage 11.

The holder 21 is configured in such way that it supports the entire underside of the wafer W so as to preserve the surface accuracy of the wafer W. As a result, it is possible to maintain a constant detection accuracy for defects on the surface of the wafer W.

The elevation mechanism 22 protrudes so that it may freely move in and out of the holder 21, and has suction attachment for freely releasing the wafer W which has been transferred by the transfer slider 12.

The tilting mechanism is constructed so that by tilting the holder 21 about a rocker shaft 20 the wafer W held by the holder 21 is tilted to an optional angle.

Figure 3:
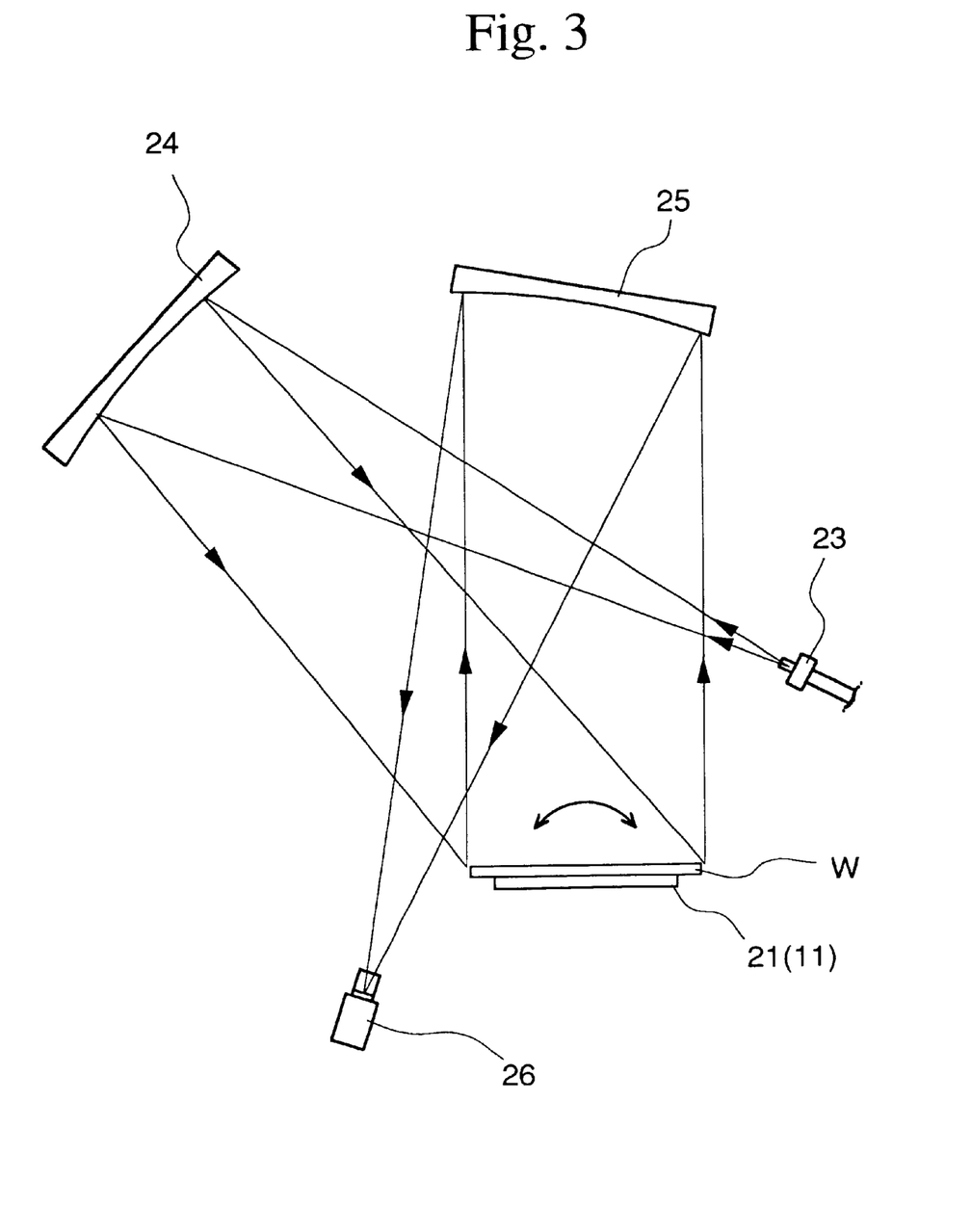
FIG. 3 is a front view showing the diffraction inspection stage in FIG. 1 provided with a light source, a concave mirror and a CCD camera.

Furthermore, as shown in FIG. 3, affixed in close proximity to the diffraction inspection stage 11 are a light source 23, concave mirrors 24 and 25, and a CCD camera 26 (photographing device). The light source 23, as with the light source 1.6, projects white light (illumination light) from a metal hydride lamp or the like, towards the concave mirror 24. The concave mirror 24 is located to the side of the diffraction inspection stage 11, and reflects the white light projected from the light source 16, towards the holder 21 on the diffraction inspection stage 11. The concave mirror 25 is located above the diffraction inspection stage 11 and reflects so that the diffracted light generated when the light source 23 illuminates the wafer W via the concave mirror 24, is focused at the CCD camera 26. The CCD camera 26 photographs the diffracted light which is reflected by the concave mirror 25.

The transfer slider 12 transfers the wafer W between the scattering inspection stage and the diffraction inspection stage 11, and comprises a guide 27 which is located along the X direction, and a suction attachment arm 28 which is mounted so as to move freely along the guide 27.

Figure 4:
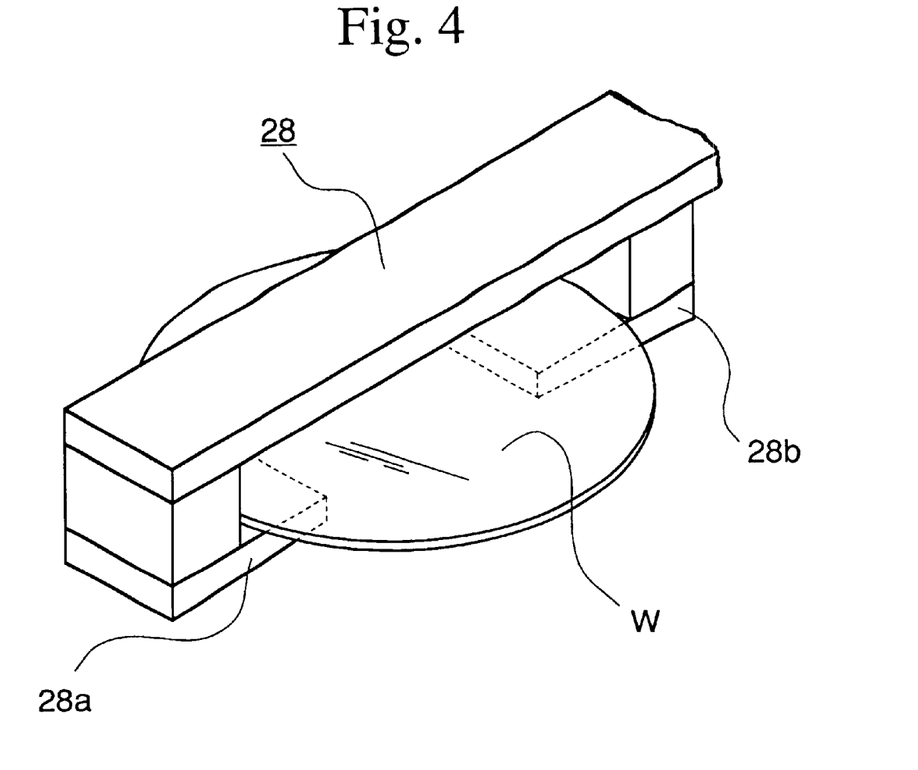
FIG. 4 is an external perspective view of a suction attachment arm which constitutes the appearance inspection apparatus of the present invention.

As shown in FIG. 4, suction attachment parts 28a and 28b, which are sited at a constant distance from the suction attachment arm 28, are located on the under the suction attachment arm 28. Both the suction attachment parts 28a and 28b are configured in such a way that they catch and suction to the opposite edges of the wafer W. Furthermore, a central position between the suction attachment parts 28a and 28b, and a central position of the scattering inspection stage 10 and the diffraction inspection stage 11 are aligned in an approximate straight line along the X direction.

A method for conducting an appearance inspection of the wafer W using the appearance inspection apparatus as comprised above, will be explained first using the example when the wafer W is one piece.

Firstly, the wafer W being the object to be inspected, is set on the support base 6 of the carrier set section 2 while being stored in the carrier 5. At this point, the direction of the notch (or the orientation flat) with respect to a pitch of a line and space pattern on the wafer W is already known, and has been input to the main control section. Furthermore, the angle of inclination for the wafer W to satisfy the diffraction condition corresponding to this pattern, is also input in advance to the main control section for each wafer.

Next, the suction attachment arm 8 on the transfer robot 7 suction attaches and takes out a predetermined wafer W from the carrier 5, and mounts the wafer W on the scattering inspection stage 10 by entering the main body cover 9 in the inspection section 4 by way of the shutter 13. At this point, since the shutter 13 which is linked to the transfer robot 7, opens its aperture, the transfer of the wafer W is executed without a delay. Then, with the completion of the transfer of the wafer W. the transfer robot 7 retracts from the main body cover 9 whereupon the shutter 13 closes and the inside of the main body cover 9 is maintained in darkness.

When the wafer W is mounted onto the scattering inspection stage 10, the step of aligning the wafer W is carried out prior to the inspection thereof. In other words, the inspection stage 10 moves towards the edge detection section 19 on the alignment mechanism 15 at the same time as rotating. At this point, the edge detection section 19 detects the direction and central position of the wafer W from the positions of the edge and notch (or the orientation flat) on the rotating wafer W.

Then, the stage control section rotates the scattering inspection stage while moving it in a horizontal direction so that the center of the wafer W comes to a predetermined position of the inspection position K and also so that the wafer W is at a predetermined direction with respect to the light source 16. At this time, since the horizontal movement and the rotation are carried out simultaneously, it is possible to reduce the amount of time required to position the wafer W.

When the wafer W is set in a predetermined position of the inspection position K, the scattering inspection, being the first step (one step), is executed. In other words, as shown in FIG. 2, white light is projected from the light source 16 and illuminates the whole surface of the wafer (omitted from FIG. 2) on the scattering inspection stage 10 at a slight angle close to parallel with the surface of the wafer. At this time, when defects such as scratches, and impurities exist on the wafer W, scattered light is generated at those locations. The scattered light is reflected by the concave mirror 17 and is imaged and photographed by the CCD camera 18. Then, an electrical signal which contains information about the scattered light is output to the main control section.

The main control section performs image processing based on the input electrical signal and detects the size and lighting of the defects along with their coordinates, and by comparing these with a predetermined threshold, determines whether diffraction inspection for this wafer W will be executed or cancelled. At this point, in cases where the defects exceed the predetermined threshold, it is decided to cancel the diffraction inspection for this wafer W.

Furthermore, when there is a possibility that there is coating unevenness or the like on the resist, although the defects which have been detected in the scattering inspection step do not exceed the predetermined threshold, a weighting corresponding to this possibility is performed with respect to the coordinates of the defects, and an additional inspection mode is instituted in the main control section.

In this manner the scattering inspection step is completed.

Moreover, depending on the wafer W, the scattering inspection stage 10 may be rotated a second time and a direction different from that mentioned above set, so that for one wafer W a plurality of scattering inspections can be performed.

When the scattering inspection step is completed, the wafer W is pre-aligned in the direction required for the diffraction inspection step being the second step (other step) by using position information for the direction of the wafer W detected in the alignment step, and by rotating the scattering inspection stage 10 while the wafer W is still mounted thereon. Moreover, in cases where it has been determined during the scattering inspection step that the diffraction inspection of the wafer W is to be cancelled, this alignment does not take place.

When the alignment of the wafer W has been completed, a transfer step in which the wafer W is transferred, commences so that the diffraction inspection step follows the scattering inspection step. In other words, firstly the scattering inspection stage 10 moves upwards so that the height of the wafer W sits between the suction attachment arm 28 and the suction attachment parts 28a and 28b. Next, when the suction attachment arm 28 of the transfer slider 12 shifts to the inspection position K of the scattering inspection stage 10 along the guide 27, the scattering inspection stage 10 descends. As a result of this, the suction attachment parts 28a and 28b suction attach and hold so that they attach to the opposite edges of the wafer W.

Under these conditions, the suction attachment arm 28 is shifted along the X direction and is positioned above the holder 21 of the diffraction inspection stage 11. At this point, the holder 21 is put in a horizontal position and the elevation mechanism 22 protrudes above the holder 21 and suction attaches the wafer W which is being held by the suction attachment parts 28a and 28b of the suction attachment arm 28. After the suction attachment arm 28 is retracted, the elevation mechanism 22 is lowered, and the wafer W is mounted on the holder 21. In this way, the wafer W is transferred from the scattering inspection stage 10 to the diffraction inspection stage 11, whereby the transfer step is completed.

Here, in cases where during the scattering inspection step it has been decided to cancel the diffraction inspection of the wafer W, the transfer robot 7 moves to a position facing the shutter 14, and immediately takes the wafer W out of the diffraction inspection stage 11 by way of the aperture and stores this in a predetermined carrier 5.

In contrast, in the case where it has been decided to execute the diffraction inspection step of the wafer W, the diffraction inspection step commences. When the wafer W is set in the holder 21, the holder 21 tilts about the rocker shaft 20 by means of the tilting mechanism, whereby the wafer W is inclined to an inclination angle which satisfies the diffraction condition. Then, as shown in FIG. 3, when the white light is projected from the light source 23 this white light is reflected by the concave mirror 24 and telecentrically illuminates the whole of the wafer W on the holder 21 on the diffraction inspection stage 11 (omitted from FIG. 3).

The diffracted rays which are generated at this time are reflected by the concave mirror 25 and an image is captured on the CCD camera 26. Then, an electric signal which includes information relating to the diffracted light is output to the main control section.

The main control section carries out image processing based on the input electric signal, and detects the size and lighting of defects as well as the coordinates thereof.

While at this point the diffraction inspection step would normally be completed, at times when the additional inspection mode has been instituted in the main control section, the inspection mode is altered and additional inspections are carried out. In other words, as well as searching for an effective inclination angle for the coordinate position of possible defects for carrying out the diffraction inspection, the tilting mechanism is activated and the holder 21 tilts so that the wafer W lies at this inclination angle. After this, in the same way as described above, the diffraction inspection of the wafer W is implemented and re-inspection takes place concentrating on positions which were detected during the scattering inspection as likely to contain surface defects or the like.

Moreover, in relation to this additional inspection mode, a second diffraction inspection may be performed without changing the inclination angle so as to raise the gain value of the electrical signal which includes information on the diffracted light. Furthermore, in relation to the electrical signals obtained from the first inspection, it is acceptable to not carry out a further inspection but to amplify the signal corresponding to the positions that have been detected as likely to have surface defects or the like.

Moreover, in cases where the additional inspection mode in the main control section has not been instituted, the holder 21 is tilted again and by setting an inclination angle that is different from that described above, it is possible to carry out the diffraction inspection a plurality of times on one wafer W.

When the diffraction inspection step has been completed, as described above the transfer robot 7 shifts to a position facing the shutter 14, and the shutter 14 opens. Then, the suction attachment arm 28 enters the main body cover 9 by way of the aperture, and after suction attaching the wafer W, retracts from the main body cover 9. The retraction of the suction attachment arm 28 is accompanied by the closing of the shutter 14, whereby a darkened condition is maintained within the main body cover 9.

After this, the transfer robot 7 moves to a position facing the carrier 5, within which the transferred wafer W has been stored, and the wafer W is stored in the slot where it was originally stored.

Moreover, it is also acceptable to arrange a carrier dedicated to wafers which have completed the scattering inspection and the diffraction inspection and to successively store the wafers in this carrier upon completion of the inspections without returning the wafer W to the original position thereof. Furthermore, it is acceptable to separately arrange dedicated carriers for waters which have been deemed unusable during the inspection.

Following on this, a method for carrying out the appearance inspection of a plurality of wafers using the appearance inspection apparatus described above will now be explained. Here although there are no diagrams for this, the wafers are numbered W1, W2, . . . , in the order in which they are transferred to the inspection section 4.

When the transfer robot 7 retracts from the main body cover 9 after it has mounted the wafer W1 on the scattering inspection stage 10, a new wafer W2, is taken out of the carrier 5 and waits in front of the shutter 13.

When the scattering inspection for the wafer W1 has been completed and the wafer W1 has been transferred from the scattering inspection stage 10 to the diffraction inspection stage 11 by the transfer slider 12, the transfer robot 7 transfers the next wafer W2, and mounts it on the scattering inspection stage 10 on which there is no wafer mounted. At this point the shutter 13 opens.

After this, the diffraction inspection of the wafer W1 which has been transferred to the diffraction inspection stage 11, and the scattering inspection of the next wafer W2 which has been transferred to the scattering inspection stage 10 are both carried out concurrently in the inspection section 4. While this is taking place the transfer robot 7 shifts to a position facing the shutter 14 in order to take out the wafer W1 when the diffraction inspection has been completed.

Figure 5:
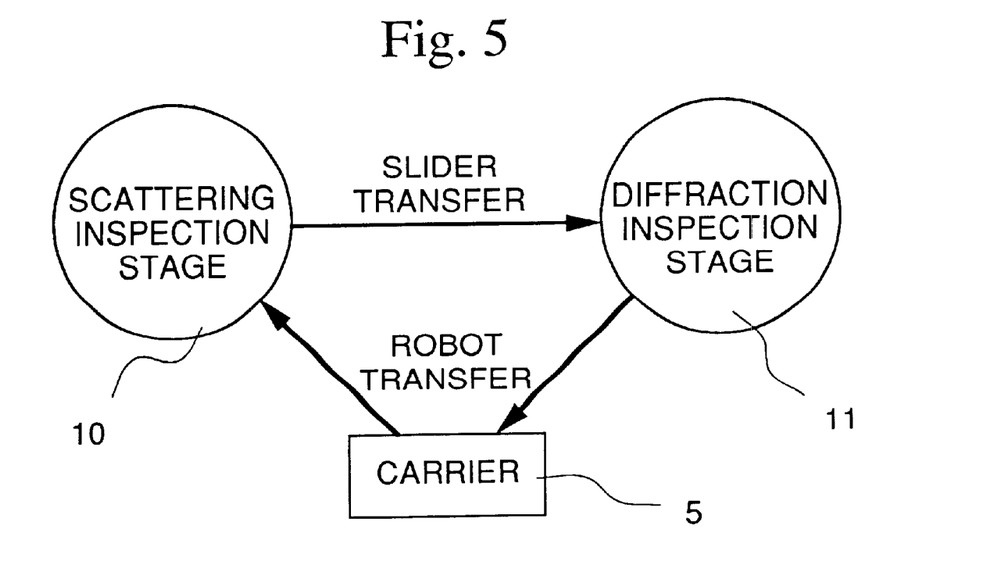
FIG. 5 is a concept diagram showing an inspection sequence for a wafer in the first embodiment of the present invention.

Then, when the inspections in the inspection section 4 have been completed, the transfer robot 7 takes the wafer W1 out of the diffraction inspection stage 11 and stores it in the predetermined carrier 5. At the same time, the transfer slider 12 transfers the wafer W2, which is on the scattering inspection stage 10, to the diffraction inspection stage 11, and the transfer robot 7 takes the next wafer W3 from the carrier 5 and transfers it to the scattering inspection stage 10. Then, this sequence is repeated in succession for further wafers. from wafer W4 onwards. An abbreviated version of this sequence is shown in FIG. 5.

The wafers which have completed inspection are transferred together with the carriers 5, and a subsequent inspection step, for example a superposition inspection, is carried out.

With the appearance inspection method and the appearance inspection apparatus of the present embodiment, since a scattering inspection step and a diffraction inspection step are provided and also a transfer step whereby the transfer slider 12 transfers the wafer between the stage 10 and the stage 11 which perform different inspections, then while maintaining the same functions as for inspections which used to be carried out visually, it is possible to prevent a lengthening in throughput time even while automating a plurality of inspections.

Furthermore, with the appearance inspection method and the appearance inspection apparatus of the present embodiment, since corresponding to the transfer of the wafer W1 from the scattering inspection stage 10 to the diffraction inspection stage 11, a new wafer W2 is transferred to the scattering inspection stage 10, it is possible to implement the scattering inspection step and the diffraction inspection step concurrently and simultaneously, thereby enabling a significant increase in inspection throughput.

In addition, with the appearance inspection method and the appearance inspection apparatus of the present embodiment, since in the diffraction inspection stage 1 the construction is such that the light source 23 and the concave mirrors 24 and 25 are fixed and the wafer W is tilted, then in addition to making it possible to raise throughput markedly in comparison to cases where the wafer W is fixed and the light source 23 and the concave mirrors 24 and 25 are moved together by a plurality of mechanisms, it is also possible to contribute towards eliminating dust.

Furthermore, with the appearance inspection method and the appearance inspection apparatus of the present embodiment, since through the alignment step prior to the scattering inspection, the wafer W is positioned at a direction depending on the pattern thereof, it becomes possible to carry out inspection at the optimum position corresponding to the wafer W. Moreover, as well as improving the accuracy of the inspection not only is the presence of defects detected easily through the inspection, but it is also possible to specify the coordinate position of any defects that may occur, so that it is possible afterwards to easily undertake a so-called micro inspection whereby such locations are inspected thoroughly.

Furthermore, since upon completion of the scattering inspection it is possible to pre-align the wafer W to the position required for the diffraction inspection by rotating the wafer while mounted on the scattering inspection stage 10, inspection at the optimum position corresponding to the wafer W (for example, corresponding to the array direction of the pattern on the wafer W) becomes possible also in the diffraction inspection, enabling an improvement in inspection accuracy, as well as making it possible to specify the coordinate position of any defects that occur, in the same way as with the scattering inspection, so that it is also possible to easily carry out a micro inspection after the diffraction inspection. In addition, since it is no longer necessary to provide a mechanism for separate alignment for the diffraction inspection stage, it is possible to also realize device miniaturization and a reduction in costs.

Moreover, with the appearance inspection method and the appearance inspection apparatus of the present embodiment, when based on the inspection results from the scattering inspection there is the possibility of surface defects on the resist on the wafer W, since an additional inspection mode is instituted in addition to the normal diffraction inspection, whereby the diffraction inspection is carried out with particular focus on those locations where defects are likely, it is possible to also reliably detect even smaller defects and thereby improve the inspection accuracy.

Furthermore, with the appearance inspection method and the appearance inspection apparatus of the present embodiment, in the case where based on the inspection results of the scattering inspection the size of the defects exceed the threshold, the construction is such that the diffraction inspection is cancelled. Hence it becomes possible to remove a redundant step of performing a diffraction inspection on a wafer which is unusable, thereby enabling an improvement in throughput. Furthermore, since the wafer W whose diffraction inspection has been cancelled is not directly taken from the inspection section 4 from the scattering inspection stage 10, but is taken out once by way of the diffraction inspection stage 11, there is no interruption of the sequence of the wafer transfer shown in FIG. 5, enabling execution of the inspection as prescribed.

Furthermore, according to the appearance inspection apparatus of the present embodiment, since the shutters 13 and 14 are provided in the aperture through which the wafer W passes when it is transferred by the transfer robot 7, then at the time of inspection it is possible to maintain darkness within the main body cover 9. Moreover, it is possible to minimize the influence of any stray light from outside the device, thereby leading to an improvement in inspection accuracy.

Figure 6:
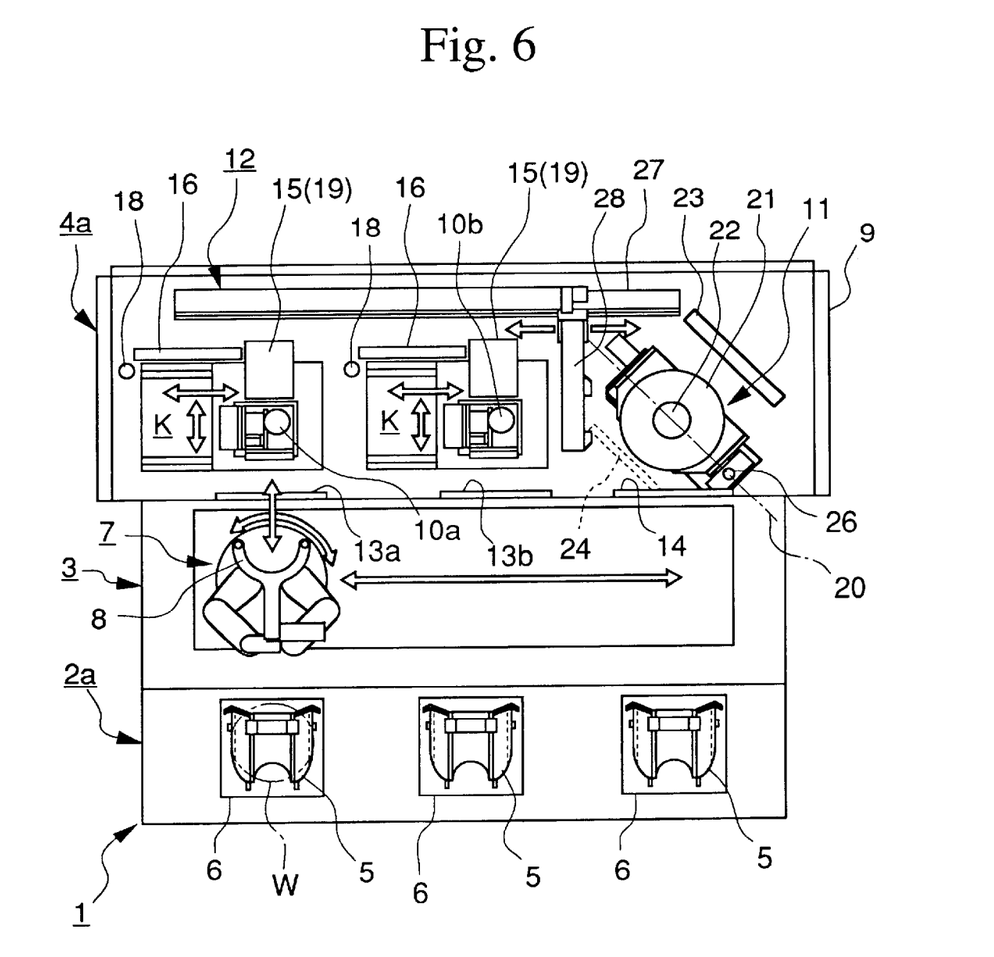
FIG. 6 is a diagram of a second embodiment of the present invention, being a plan view of an appearance inspection apparatus provided with two scattering inspection stages for one diffraction inspection stage.

Next, FIG. 6 is a diagram showing a second embodiment of an appearance inspection apparatus of the present invention.

In this figure, the same reference numerals are attached to those elements which are identical to the elements in the first embodiment shown in FIG. 1 through FIG. 5, and explanation thereof is omitted.

The points of difference between the second embodiment and the first embodiment as shown above are the construction of the carrier set section and the inspection section.

In other words, in the carrier set section 2a there are the three support platforms 6 positioned at intervals along the X direction, for supporting the carriers 5 in located conditions.

Furthermore, in the inspection section 4a there are two scattering inspection stages 10a and 10b positioned one after the other in the X direction inside the main body cover 9. Attached to each of the scattering inspection stage 10a and 10b are their respective alignment mechanisms 15, light sources 16, concave mirrors 17 (not shown in FIG. 6) and CCD cameras 18.

On the surface of the wall on the transfer section 3 side of the main body cover 9 there are positioned respectively apertures (not shown) and shutters 13a, 13b and 14 which freely open and close the apertures and which face the scattering inspection stages 10a and 10b and the diffraction inspection stage 11. Furthermore, the transfer robot 7 is made such that it may move freely to positions facing the shutters 13a, 13b and 14 respectively. In the same way, as with the transfer slider 12, as the suction attachment arm 28 moves along the guide 27 it is possible for it to access each of the shutters 13a, 13b and 14. Other construction is the same as for the first embodiment mentioned above.

The method for carrying out the appearance inspection using the appearance inspection apparatus 1 of the above construction will now be explained.

Here, the explanation will use an example for the case where, when the time required for the diffraction inspection of one wafer is one unit of time, the scattering inspection time per one wafer which includes the alignment step, requires a double unit of time. Furthermore, in the same way as above, the wafers W1, W2, . . . , will be numbered according to the order in which they are transferred to the inspection section 4a.

Firstly, the transfer robot 7 takes a predetermined wafer W1 out of the carrier 5 and mounts it on the scattering inspection stage 10a by way of the shutter 13a. When the transfer robot 7 retracts from the inside of the main body cover 9, the scattering inspection of the wafer W1 is carried out after the alignment step has been completed.

Meanwhile, the transfer robot 7 takes the wafer W2 out of the carrier 5 and mounts it on the scattering inspection stage 10*b* by way of the shutter 13*b*. When the transfer robot 7 retracts from the inside of the main body cover 9, the scattering inspection of the wafer W2 is carried out after the alignment step has been completed. At this time, the timing for transferring the wafer W2 is adjusted so that with the wafer W1 on the scattering inspection stage 10*a*, almost half of the step has been completed.

Furthermore, when the inspection of the wafer W1 is completed taking a double unit of time, the transfer slider 12 transfers the wafer W1 to the diffraction inspection stage 11. This is accompanied by the transfer to the scattering inspection stage 10*a* of the next wafer W3, by the transfer robot 7. When the wafer W3 is set on the scattering inspection stage 10*a*, the alignment of the wafer W3 and the diffraction inspection of the wafer W1 on the diffraction inspection stage 11 are commenced almost simultaneously. At this time, about half of the inspection for the wafer W2 on the scattering inspection stage 10*b* has been completed.

With the passing of almost one unit of time from this point, both the scattering inspection of the wafer W2 on the scattering inspection stage 10*b* and the diffraction inspection of the wafer W1 on diffraction inspection stage 11 are completed almost simultaneously. Furthermore, at the same time as the transfer robot 7 takes the wafer W1 from the diffraction inspection stage 11 by way of the shutter 14 and stores it in the carrier 5, the transfer slider 12 transfers the wafer W2 which is on the scattering inspection stage 10*b*, to the diffraction inspection stage 11.

At this point, when the transfer robot 7 stores the wafer W1 in the carrier 5. it immediately takes the next wafer W4, from the carrier 5 and transfers it to the scattering inspection stage 10*b* by way of the shutter 13*b*. The inspection of the wafer W3 on the scattering inspection stage 10*a* is about half completed. This is then followed by the repetition of the actions mentioned above in that order.

In this way, with the appearance inspection method and the appearance inspection apparatus of the present embodiment, in addition to obtaining the same results as for the first embodiment described above, in cases where the scattering inspection step which takes a long amount of inspection time is followed by the diffraction inspection step which takes a short inspection time, a plurality of diffraction inspection steps are carried out concurrently with respect to the scattering inspection step. Moreover, in the transfer step, by transporting from the wafer which has completed the scattering inspection step so as to sequentially carry out the diffraction inspection, it unnecessary to adjust the period for carrying out the diffraction inspection step to suit the period for the scattering inspection step which has a long inspection time. Hence it is possible to set up a short inspection time and thus enable an even shorter time taken for throughput.

Figure 7:
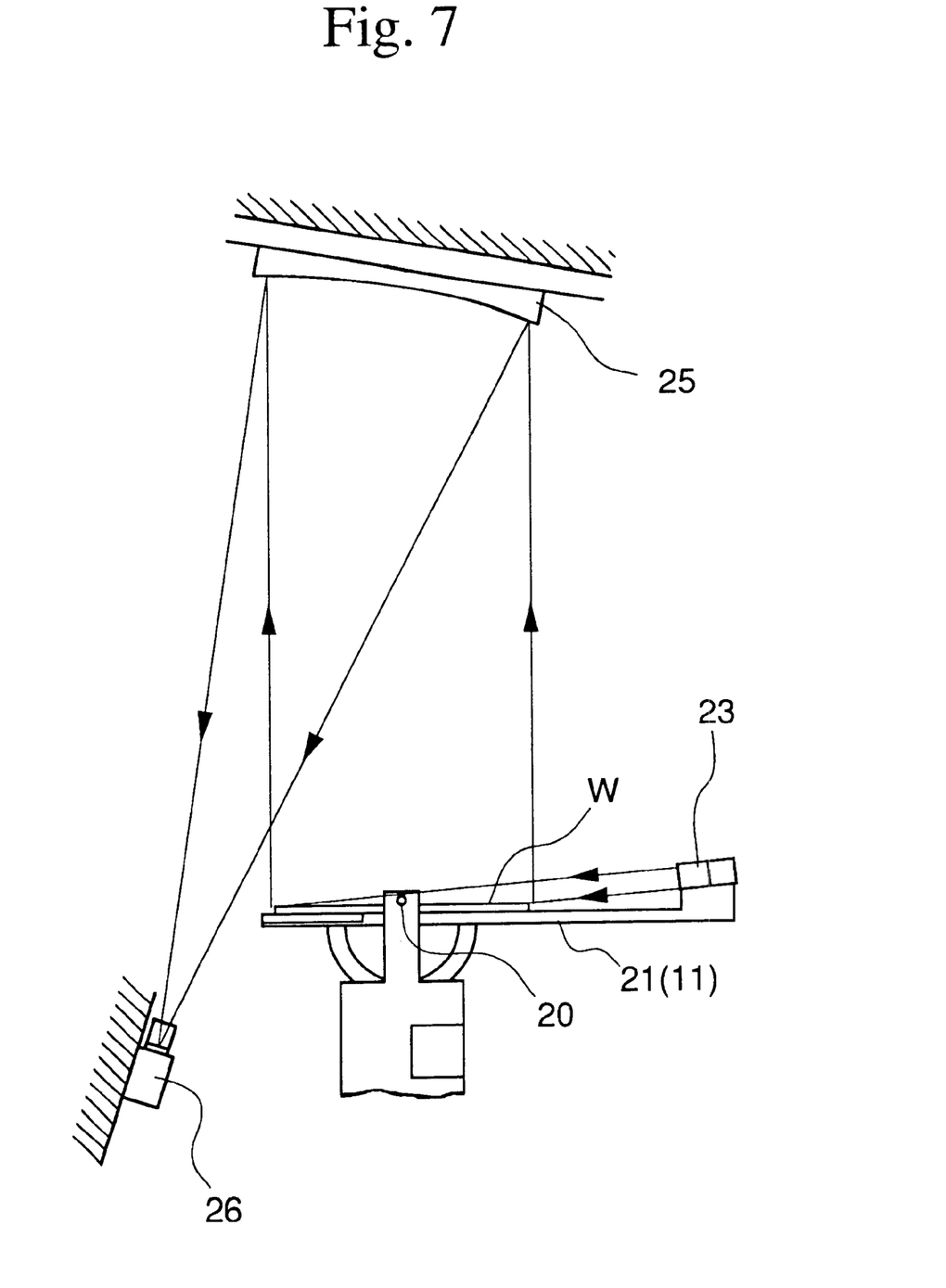
FIG. 7 is a front view showing another example of a diffraction inspection stage.

Moreover, with regard to the embodiment described above, while it is constructed so that the holder 21 in the diffraction inspection stage 11 and the light source 23 are fixed independently, a construction is also possible where the light source 23 is fixed on top of the holder 21 as shown in FIG. 7. In this case, the angle of incidence of the white light from the light source 23 is set at between 80° and 89° with respect to the normal to the surface of the wafer on the holder 21. Furthermore, the construction is such that it is possible to tilt both the wafer W and the light source 23 on the holder 21 together about the rocker shaft 20.

Figure 8:
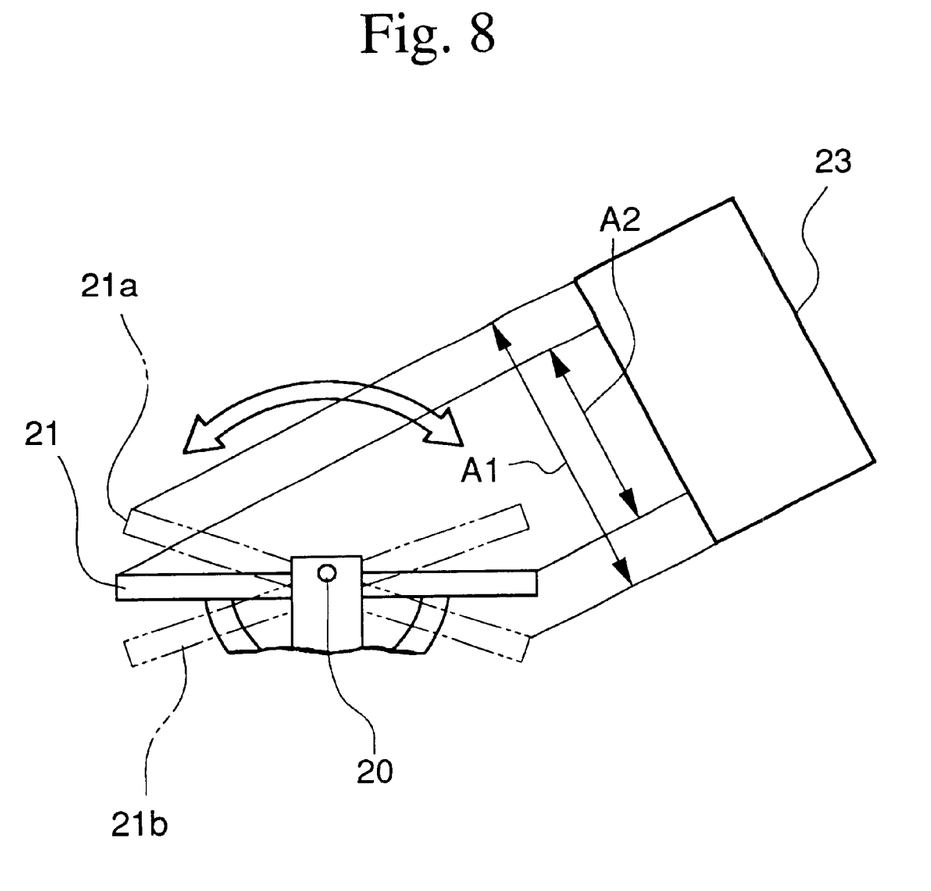
FIG. 8 is a front view showing a conventional holder and light source.

Heretofore, as shown in FIG. 8, since it is possible to tilt the holder 21 from the inclined position 21*a* to the inclined position 21*b* via the horizontal condition, it is necessary that the light source 23 projects white light to the illumination area A1 so that the whole of the wafer W on the holder 21, which lies for example at the inclined position 21*a*, is illuminated. However, since when the holder 21 is in a horizontal position it is sufficient to project white light to only the illumination area A2, the part outside the illumination area A2 becomes redundant.

Therefore, at times of inspection under predetermined diffraction conditions, such as a slight angle of incidence, by constructing the light source 23 and the holder 21 together as one as shown in FIG. 7, the angle of incidence and the amount of incident light is always constant for the wafer W on the holder 21, so that it is possible to illuminate an appropriate illumination area with no loss. Furthermore, by optionally setting the light receiving angle of the CCD camera 26 and photographing the diffracted light at an angle which satisfies the conditions for diffraction, it is also possible to photograph the scattered light at an angle that does not satisfy the conditions for diffraction.

Furthermore, with the embodiment described above, although constructed such that the light sources 16 and 23, which project the white light serving as the illumination light, are separately provided, it is also possible to provide a beam splitter whereby a single light source is shared. In this case, since the number of light sources is reduced, miniaturization of the device and a reduction in costs can be realized.

Furthermore, with the embodiment described above, although constructed such that the diffraction inspection step takes place after the scattering inspection step, the construction is not limited to this, and by providing the alignment mechanism 15 in the diffraction inspection stage 1, the scattering inspection step can be performed after the diffraction inspection step.

A construction is also possible where a barcode for distinguishing one wafer from another is affixed to the wafer W, and a barcode reader is attached to either the transfer robot 7 or the transfer slider 12 so that the direction or the like, for the notch (or orientation flat) with respect to the pitch which is input to the main control section in advance is read.

Furthermore, while the construction is such that the wafer W is rotated on the scattering inspection stage 10 in advance to give the required direction for the diffraction inspection, the construction may be such that a rotation mechanism is added for example to the elevation mechanism 22, so that this rotation mechanism aligns the wafer W with a predetermined direction. In this case, at times when inspection at a plurality of directions is necessary such as when logic is included in the circuit pattern, versatility is enhanced by being able to set a plurality of directions.

In addition, as a construction where shutters are provided for performing an opening and closing operation accompanying the movement of the transfer slider 12 between the scattering inspection stage 10 and the diffraction inspection stage 11, the construction may be such that the white light used in the respective inspections does not influence any of the inspections as stray light.

Furthermore, although the construction is such that the transfer slider 12 is used as a means of transfer in the transfer step, the construction is not restricted to this, and a construction is also possible where for example, the transfer robot 7 is used to transfer the wafer W between the scattering inspection stage 10 and the diffraction inspection stage 11.

Moreover, though the objects to be inspected have been wafers used in the manufacture of semiconductor devices, the objects to be inspected are not restricted to wafers and the present invention is also applicable to the inspection of, glass substrates used in liquid crystal display devices, thin film magnetic heads, imaging elements (CCDs), masks and the like. In this regard, for objects to be inspected which have a wide surface area such as glass substrates, the whole surface is not illuminated together, but rather it is possible to adopt a scanning illumination method where the object to be inspected is moved relative to the light source, the concave mirror or the CCD, or a method which illuminates the object to be inspected while being successively moved stepwise.

What is claimed is:

1. An appearance inspection method comprising:
    a first step in which an object to be inspected is inspected by illuminating said object mounted on a first stage and receiving scattered light therefrom,
    a second step in which said object to be inspected is inspected by illuminating said object mounted on a second stage and receiving diffracted light therefrom, and
    a transfer step in which said object to be inspected is transferred between said first stage and said second stage so that either one of said first step and said second step is carried out after the other;
    wherein in at least one of said first step and said second step, prior to inspection of said object to be inspected, an alignment step is carried out for aligning said object to be inspected at a predetermined location by moving at least one of said first stage and said second stage.

2. An appearance inspection method according to claim 1, wherein in accordance with the transfer by said transfer step of said object to be inspected from one stage of said first step and said second step, a new object to be inspected is transferred to said one stage.

3. An appearance inspection method according to claim 1, wherein said alignment step is carried out in one of said first step or said second step, and after completion of said first step or second step, said object to be inspected, while remaining mounted on the stage used for said first step or second step, is pre-aligned to a direction required for the other step of said first step or said second step using position information obtained in said alignment step for said object to be inspected, after which said object to be inspected is transferred to the stage of said other step by said transfer step.

4. An appearance inspection method according to claim 1, wherein in the case where after a long inspection time step which is carried out in one of said first step or said second step and requires a longer time than the other step of said first step and said second step, a short step which is said other step, is carried out, a plurality of said long inspection time steps are carried out concurrent with said short step, and said transfer step transfers so that said object to be inspected which has just completed said long inspection time step is transferred to said short steps one after another.

5. An appearance inspection method according to claim 1, wherein based on inspection results for said object to be inspected in one of said first step or said second step, an inspection mode for the other of said first step and said second step is changed.

6. An appearance inspection method according to claim 1, wherein in accordance with inspection results for said object to be inspected in one of said first step or said second step, a decision is made to either execute or cancel the other step of said first step and said second step for said object to be inspected.

7. An appearance inspection method according to claim 6, wherein in the case where said other step is cancelled in accordance with the inspection results for said object to be inspected, said object to be inspected is transferred by way of said first stage or said second stage used in said other step.

8. An appearance inspection apparatus comprising:
    a first stage that inspects an object to be inspected by illuminating said object to be inspected and receiving scattered light therefrom,
    a second stage that inspects said object to be inspected by illuminating said object to be inspected and receiving diffracted light therefrom, and
    a transfer mechanism that transfers said object to be inspected between said first stage and said second stage so that either one of the inspection of said first stage and the inspection of said second stage is carried out after the other;
    wherein in at least one of said first stage and said second stage, an alignment mechanism is provided for performing alignment of said object to be inspected by moving at least one of said first stage and said second stage.

9. An appearance inspection apparatus according to claim 8, wherein the illumination light used for said first stage and the illumination light used for said second stage share a single light source.

* * * * *